(12) United States Patent
Nishida

(10) Patent No.: US 12,152,234 B2
(45) Date of Patent: Nov. 26, 2024

(54) METHOD OF SCREENING CO2-ASSIMILATING MICROORGANISM

(71) Applicant: HITACHI, LTD., Tokyo (JP)

(72) Inventor: Hirokazu Nishida, Tokyo (JP)

(73) Assignee: HITACHI, LTD., Tokyo (JP)

( * ) Notice: Subject to any disclaimer, the term of this patent is extended or adjusted under 35 U.S.C. 154(b) by 169 days.

(21) Appl. No.: 17/586,587

(22) Filed: Jan. 27, 2022

(65) Prior Publication Data

US 2022/0298498 A1      Sep. 22, 2022

(30) Foreign Application Priority Data

Mar. 22, 2021   (JP) ................. 2021-046937

(51) Int. Cl.
*C12N 15/01* (2006.01)
*C12N 1/02* (2006.01)
*C12N 1/20* (2006.01)

(52) U.S. Cl.
CPC ............... *C12N 15/01* (2013.01); *C12N 1/02* (2013.01); *C12N 1/20* (2013.01)

(58) Field of Classification Search
CPC .............. C12N 15/01; C12N 1/02; C12N 1/20
See application file for complete search history.

(56) References Cited

U.S. PATENT DOCUMENTS

| | | | |
|---|---|---|---|
| 6,830,899 B1 | 12/2004 | Chen et al. | |
| 2010/0112647 A1 | 5/2010 | Hara et al. | |
| 2016/0160250 A1 | 6/2016 | Jung et al. | |

FOREIGN PATENT DOCUMENTS

| | | |
|---|---|---|
| CN | 101412965 A | 4/2009 |
| EP | 1170358 A1 | 1/2002 |
| JP | S54-119091 A | 9/1979 |
| JP | S62-236479 A | 10/1987 |
| JP | H03-67581 A | 3/1991 |
| JP | 2002-017342 A | 1/2002 |
| JP | 2018139507 A | 9/2018 |
| WO | 2004085627 A1 | 10/2004 |

OTHER PUBLICATIONS

Charles HP, Roberts GA. Carbon dioxide as a growth factor for mutants of Escherichia coli. J Gen Microbiol. Apr. 1968;51(2):211-24. (Year: 1968).*
Shari et al.: Mutagenesis on Cyanobacteria for High CO2 Uptake: A Review J Pure Appl Microbio, 8(SPL. Edn.), May 2014. (Year: 2014).*
Mehta K, Jaiswal D, Nayak M, Prasannan CB, Wangikar PP, Srivastava S. Elevated carbon dioxide levels lead to proteome-wide alterations for optimal growth of a fast-growing cyanobacterium, Synechococcus elongatus PCC 11801. Sci Rep. Apr. 18, 2019;9(1):6257. (Year: 2019).*
Antonovsky N, Gleizer S, Noor E, Zohar Y, Herz E, Barenholz U, Zelcbuch L, Amram S, Wides A, Tepper N, Davidi D, Bar-On Y, Bareia T, Wernick DG, Shani I, Malitsky S, Jona G, Bar-Even A, Milo R. Sugar Synthesis from CO2 in *Escherichia coli*. Cell. Jun. 30, 2016;166(1):115-25. (Year: 2016).*
Zhu et al., "Collaborative regulation of CO2 transport and fixation during succinate production in *Escherichia coli*" Scientific Reports 5:17321 (2015).
Gleizer et al., "Conversion of *Escherichia coli* to Generate All Biomass Carbon from CO2" Cell 179:1255-1263 (2019).
Zhang et al., "Metabolic evolution of energy-conserving pathways for succinate production in *Escherichia coli*" PNAS USA 106(48):20180-20185 (2009).
Donnelly et al., "A Novel Fermentation Pathway in an *Escherichia coli* Mutant Producing Succinic Acid, Acetic Acid, and Ethanol" Appl. Biochem. Biotech. 70-72:187-198 (1998).

* cited by examiner

*Primary Examiner* — Allison M Fox
*Assistant Examiner* — Qinhua Gu
(74) *Attorney, Agent, or Firm* — PROCOPIO, CORY, HARGREAVES & SAVITCH LLP

(57) ABSTRACT

The present invention provides a method of producing a microorganism having an ability of assimilating a first factor including: a step of subjecting a microorganism to random mutagenesis; and a step of culturing the microorganism in the presence of a highly concentrated first factor and then selecting the grown microorganism.

15 Claims, 4 Drawing Sheets

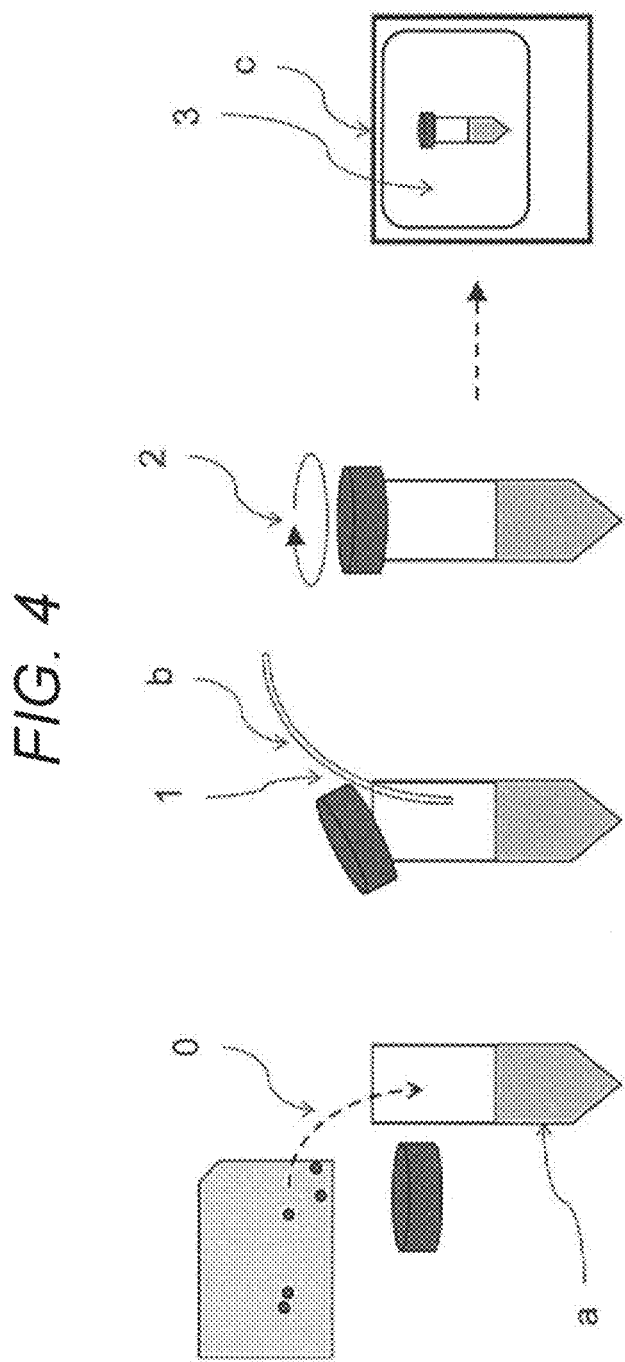

METHOD OF SCREENING CO2-ASSIMILATING MICROORGANISM

CROSS-REFERENCE TO RELATED APPLICATIONS

This application claims the benefit of priority to Japanese Patent Application No. 2021-046937 filed Mar. 22, 2021, which is hereby incorporated by reference in its entirety.

BACKGROUND OF THE INVENTION

1. Field of the Invention

The present invention relates to production of a microorganism having an ability of assimilating a target factor. More specifically, the present invention provides a method of efficiently producing and screening a microorganism such as a bacterium capable of taking $CO_2$ in the air into the cells and fixing carbon.

2. Description of the Related Art

An increase in the concentration of greenhouse gases in the atmosphere is considered to be a main factor of global warming. Particularly, $CO_2$ whose emission amount has increased exponentially in the last two centuries is mainly targeted for emission suppression. Absorption (fixation) of $CO_2$ released into the air in parallel with suppression of $CO_2$ emission has also been a pressing issue. Various $CO_2$ fixation methods have been proposed so far. A large-scale technique of depositing $CO_2$ masses in the deep seabed causes future concerns for areas surrounding Japan where the stability of the ground is problematic. Few other chemical techniques can be operated at low cost and low energy. Further, a desirable technique is such that the benefit of $CO_2$ is changed, for example, by conversion of $CO_2$ into other high-value-added products, and the benefit can be given back to society.

In recent years, with the progress of synthetic biotechnology, it has become possible to biochemically increase the added value based on various compounds using bacterial cells that can be grown at a relatively low cost and in a short time, such as *Escherichia coli* and yeasts (e.g., US 2010/112647 A1; Zhu L W, et al. (2015) Sci. Rep., 5, 17321; and Gleizer S, et al. (2019) Cell Vol. 179, pp. 1255-1263.). However, under the present circumstances, bacterial cells that can absorb $CO_2$ and can converted it into high-value-added products are under development.

A method of imparting new properties to bacterial cells includes an evolutionary molecular engineering technique targeting a specific gene (e.g., Zhang X, et al. (2009) Proc. Natl. Acad. Sci. USA Vol. 106, pp. 20180-20185 and Donnelly M I, et al. (1998) Appl. Biochem. Biotech. Vol. 70-72, pp. 187-198) and a method of inducing mutation by targeting the entire genome of bacterial cells using a chemical or ultraviolet rays (e.g., JP 2018-139507 A and US 2016/160250 A1). The evolutionary molecular engineering technique introduces a random mutation into one gene among the molecules of a specific enzyme or the like, and identifies a mutation in which the function of the enzyme is improved in a desired direction (0.01 to 1%). However, the mutation rarely occurs. Further, it is necessary to apply this technique to a plurality of enzymes involved in a reaction pathway in vivo and improve many of the enzymes in a desired direction. However, it may extremely be difficult to cooperatively modify many reactions in vivo by this technique.

Meanwhile, also in a method of subjecting bacterial cells to mutagenesis, which is a method of evolving the entire bacteria at once, it is possible to introduce mutations uniformly into the entire genome of bacteria in one trial. However, for the same reason as described above, the probability that many reactions (enzymes) in vivo evolve cooperatively is extremely rare, and the probability that a variant having a target function is generated is low.

SUMMARY OF THE INVENTION

As described above, in the conventional technique, it has been difficult to modify bacterial cells so as to cooperatively change a plurality of biochemical reaction characteristics in vivo and have a certain property.

The present inventors have found that mutated bacterial cells having a target function can be efficiently produced by subjecting bacterial cells to chemical mutagenesis or UV radiation mutagenesis under a directed evolutionary pressure. In addition, the present inventors have also found that a target variant can be easily obtained by screening as many bacterial cells as possible. The present invention has been mainly completed based on the above findings.

In one aspect, the present invention provides a method of producing a microorganism having an ability of assimilating a first factor including: a step of subjecting a microorganism to random mutagenesis; and a step of culturing the microorganism in the presence of a highly concentrated first factor and then selecting the grown microorganism. In one embodiment, the step of subjecting a microorganism to random mutagenesis may be performed in the presence of a highly concentrated first factor.

According to the method according to the present invention, a microorganism having an ability of assimilating a target factor can be efficiently and simply produced, thereby contributing to cost reduction and time reduction. Further, the microorganism produced by the present method can be a platform bacterium for producing various high-value-added molecules. Therefore, the present invention may be useful in fields such as improvement of the environment (e.g., global warming) and development of bacteria producing high-value-added molecules.

BRIEF DESCRIPTION OF THE DRAWINGS

FIG. 4 is a diagram illustrating an experimental procedure of Example 2.

DETAILED DESCRIPTION OF THE INVENTION

Figure 1:
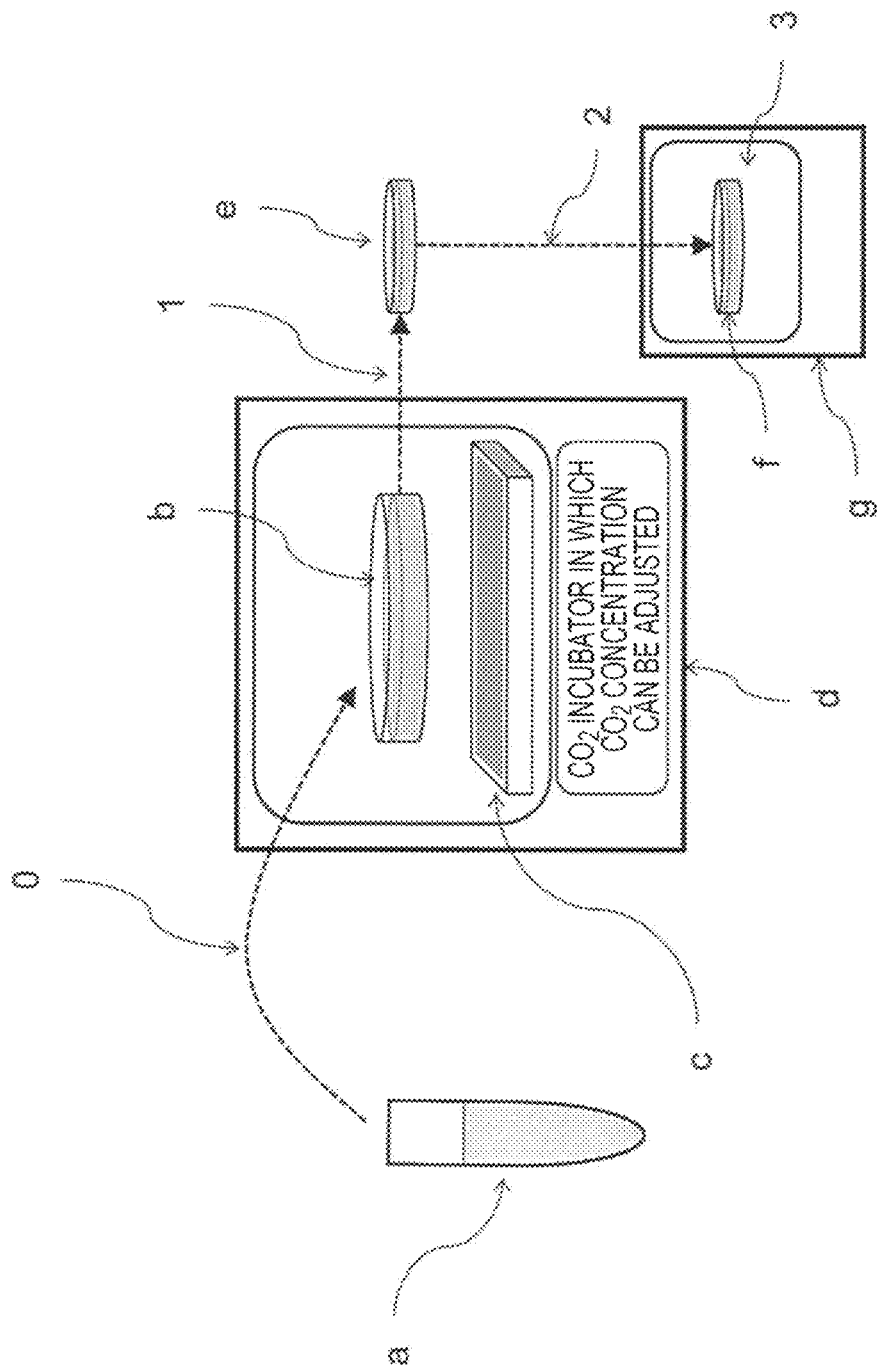
FIG. 1 is a conceptual diagram illustrating a procedure and instruments in the case of screening $CO_2$ assimilating bacterial cells while mutagenesis such as ultraviolet rays is performed under a directed evolutionary pressure in a high-concentration $CO_2$ atmosphere to which the present invention is applied.

Hereinafter, the present invention will be described in detail with reference to the drawings.

The present invention relates to production of a microorganism having an ability of assimilating a target factor (particularly, a carbon source or a nitrogen source). For example, a microorganism capable of assimilating a specific carbon source or nitrogen source can absorb the carbon source or nitrogen source, and can, if preferred, fix the carbon source or nitrogen source as a useful molecule (high-value-added molecule).

In one aspect, the present invention provides a method of producing a microorganism having an ability of assimilating a first factor including: a step of subjecting a microorganism to random mutagenesis; and a step of culturing the microorganism in the presence of a highly concentrated first factor and then selecting the grown microorganism.

The "microorganism" used herein is at least one microorganism selected from the group consisting of eubacteria, archaea, and fungi. It may be preferable to use a microorganism in which the culture method and operation method of the microorganism are known. Examples of the microorganism that can be used include, but are not limited to:

eubacteria:
  gram-negative bacteria: the genus *Escherichia*, e.g., *Escherichia coli*;
  gram-positive bacteria: the genus *Bacillus*, e.g., *Bacillus subtilis*;
  cyanobacteria: the genus *Synechococcus*, e.g., *Synechococcus elongatus*;
archaea: actinomycetes, thermophilic archaea, e.g., *Thermococcus kodakarensis* and *Pyrococcus furiosus*; and
fungi: yeasts, e.g., *Saccharomyces cerevisiae, Schizosaccharomyces pombe, Pichia pastoris*, and *Candida albicans*.

The microorganism may be a naturally occurring microorganism, an isolated microorganism, or a commercially available microorganism strain. Further, the microorganism may be a microorganism into which a genetic mutation has been introduced, and a microorganism in which a specific gene has been deleted or disrupted, or a specific gene has been introduced may be used. For example, a microorganism into which a genetic mutation involved in metabolism of the first factor has been introduced can be used, whereby a mutation considered to contribute to assimilation of the first factor can be previously introduced into the microorganism before random mutagenesis. Examples of the genetic mutation may include pyruvate carboxylase, pyruvate carboxykinase, and ribulose-1,5-bisphosphate carboxylase (RuBisCO).

The first factor used herein is a factor for which assimilability to microorganisms is desired to be imparted. Examples of the factor include, but are not limited to:

carbon sources such as carbon dioxide, carbon monoxide, methane, methanol, acetic acid, and cellulose, aromatic compounds (e.g., compounds having a benzene ring or a ring in which two or more benzene rings are condensed, including benzene, toluene, xylene, p-cresol, phenol, ethylbenzene, aniline, phenylalanine, benzyl alcohol, vanillin, phenylpropionic acid, naphthalene, and phenanthrene); and
  nitrogen sources such as nitrogen and amino acids.

According to the present invention, at least one factor selected from the group consisting of a carbon source and a nitrogen source as described above can be used as the first factor. If necessary, the first factor may be used in combination with different types of factors (e.g., a second factor and a third factor).

The term "having an ability of assimilating" means that a microorganism has an ability to take a target factor and synthesize substances such as proteins, nucleic acids, polysaccharides, and lipids using the factor.

In a method of producing a microorganism having an ability of assimilating a first factor according to the present invention (hereinafter, also referred to as "the present method"), an evolutionary molecular engineering technique is used in combination with mutagenesis in microorganisms, and a microorganism is subjected to mutagenesis under a directed evolutionary pressure, thereby producing a microorganism having an ability of assimilating a target factor. Therefore, in the present method, random mutagenesis in microorganisms and the placement of the microorganisms in the presence of a highly concentrated first factor may be performed almost simultaneously. For example, a microorganism may be subjected to random mutagenesis in the presence of a highly concentrated first factor. Alternatively, a microorganism may be cultured in the presence of a highly concentrated first factor immediately after the random mutagenesis in the microorganism.

In a preferred embodiment, a step of plating the microorganism on a plate medium may further be included before the step of subjecting a microorganism to random mutagenesis as described above. Preferably, $10^5$ or more, $10^6$ or more, $10^7$ or more, and more preferably $10^8$ or more, or $10^9$ or more microorganisms may be plated on the plate medium when the OD600 is approximately equal to 1.0-1.5 and the volume at the time of plating is 100 µL. The number of microorganisms (bacterial cells) to be plated depends on the size of the flat plate to be used and the size of the bacterial cells. In a case in which bacterial cells are seeded at the number of bacterial cells equal to or more than the number obtained by dividing the area of the plate medium by the projected area of one bacterial cell, it may be difficult to pick up the forming colonies. Thus, such number of bacterial cells can be set as the upper limit. Consequently, as many microorganisms as possible are subjected to random mutagenesis, and the selection of a clone of the microorganism having an ability of assimilating a target factor may be facilitated. The plate medium has an advantage that a large number of microorganisms can be cultured in one operation by applying (plating) the microorganisms on the surface of the plate medium (i.e., a screening population can be increased), and viable microorganisms appear as colonies, whereby it may be easy to visually select strains of the microorganisms. The plate medium is well known in the art and can be readily understood by those skilled in the art. In addition, a slant medium can also be used as the plate medium in the present invention.

For the culture of microorganisms, conventional culture conditions may be used for points other than the points described later. For example, as a medium, a medium may be used which contains a carbon source such as glucose, starch, or sucrose, and a nitrogen source such as potassium nitrate, ammonium nitrate, yeast extract, or peptone, and preferably contains inorganic salts such as potassium phosphate, magnesium nitrate, and calcium chloride, and trace components such as trace metals, amino acids, and vitamins. Those skilled in the art can select an appropriate medium depending on the type of microorganism.

A microorganism is placed in the presence of a highly concentrated first factor. The high concentration means a high concentration or abundance as compared with the concentration or abundance of the first factor in an environment in which the microorganism normally grows. For example, the high concentration may be a concentration or abundance of at least 1%, at least 3%, at least 5%, at least 8%, at least 10%, at least 15%, at least 20%, at least 25%, at least 30%, at least 40%, at least 50%, or more than the concentration or abundance of the first factor in a normal growth environment. In a case in which the first factor is not present in a normal growth environment, even a small amount of the first factor corresponds to "high concentration" in the present invention.

In the case of using carbon dioxide as the first factor, the concentration of the highly concentrated first factor can be set to, for example, a range of 400 ppm to 5000 ppm. Alternatively, in the case of using carbon dioxide as the first factor, the microorganism may be cultured in a closed incubator containing carbon dioxide at a concentration of 0.5% (w/w) to 99% (w/w), for example, a concentration of 0.5% or more, 1% or more, 3% or more, preferably a concentration of 5% or more, 10% or more, 20% or more, 30% or more, 40% or more, more preferably a concentration of 50% or more.

When the first factor is a gas, for example, a highly concentrated first factor may be introduced into a sealed container, and the microorganism may be cultured in the sealed container. When the first factor is a solid or a liquid, for example, the first factor may be added to a medium, a solution or a solid (medium, powder, granules, etc.) containing the first factor may be sprayed or layered on the medium, or a solution containing the first factor may be sprayed or layered on the microorganism on the medium, in order to culture the microorganism in the presence of a highly concentrated first factor.

Preferably, the components of the medium may be prepared such that the microorganism uses the first factor as the sole carbon or nitrogen source. For example, when the first factor is a carbon source, the microorganism may be cultured in a medium containing no carbon source other than the first factor or a medium containing only a small amount of a carbon source other than the first factor. The use of the medium allows for the isolation of, particularly, a microorganism capable of assimilating the first factor and growing, and the microorganism can efficiently assimilate the first factor.

When the microorganism is a microorganism utilizing oxygen, it may be preferable to culture the microorganism in the absence of oxygen or in the presence of a low concentration of oxygen. This makes it easy to produce a microorganism capable of assimilating the first factor particularly efficiently.

According to the method of the present invention, a microorganism may be subjected to random mutagenesis. In one embodiment, a microorganism may be subjected to random mutagenesis in the presence of a highly concentrated first factor. The term "random mutagenesis" as used herein means performing a method in which the genome of a microorganism is subjected to random mutagenesis, and the method is distinguished from site-directed mutagenesis into a specific gene of a microorganism. The random mutagenesis method is known in the art, and those skilled in the art can select an appropriate method depending on the microorganism to be used, the culture method, and the like. Examples of known random mutagenesis methods may include ultraviolet (UV) irradiation, gamma irradiation, ionizing radiation irradiation, X-ray irradiation, and addition of chemical mutagens (nitrosamine, N-ethyl-N-nitrosourea (ENU), etc.), and one of these methods or a combination of two or more of these methods can be used. It may be preferable to use ultraviolet (UV) irradiation, gamma irradiation, ionizing radiation irradiation, or X-ray irradiation, since desirable irradiation intensity and irradiation time for random mutagenesis efficiency have been frequently reported.

After the random mutagenesis, the microorganism may be cultured in the presence of a highly concentrated first factor. The culture period may vary depending on the type of microorganism to be used, and can be appropriately selected from 5 hours to several months, for example, 10 to 24 hours. In the case of using a plate medium, static culture may be performed. In the case of using other culture media, culture can be performed using various culture conditions such as static culture and shaking culture. Since the optimum conditions for culture may vary depending on the type of microorganism to be used, it may be preferable that the medium and the culture method are appropriately selected and prepared so as to be suitable for the microorganism to be used, and other culture conditions such as temperature and pH may also be appropriately selected to perform culture.

After culturing as described above, the grown microorganism may be selected. Those skilled in the art can conveniently select the microorganism depending on the type of microorganism to be used. For example, when a plate medium is used, it may be possible to select the grown microorganism as the appearance of colonies on the medium. Alternatively, it may be possible to confirm whether or not the microorganism is grown by observing a change in the culture solution, such as turbidness or discoloration.

The present method may further include a step of recovering the selected microorganism and a step of culturing the microorganism again in the presence of a highly concentrated first factor. The method of recovering the microorganism from a medium is well known in the art, and the process can be carried out by any method. The recovered microorganism may be cultured in the presence of a highly concentrated first factor using an appropriate medium. The medium to be used may be the same medium as in the case of random mutagenesis described above, or may be a different medium. For example, a plate medium may be used in random mutagenesis, and a liquid medium may be used in re-cultivation. Preferably, a medium suitable for the microorganism may be selected. The concentration of the first factor may be the same as or higher or lower than the concentration used in random mutagenesis as long as the concentration is high. The culture period and culture conditions may be appropriately selected according to the type of microorganism. By culturing in the presence of a highly concentrated first factor as described above, it may be possible to confirm that the microorganism has an ability of assimilating the first factor.

The microorganism selected as described above can grow in the presence of a highly concentrated first factor and has an ability of assimilating the first factor. In the present method, mutagenesis is performed under a directed evolutionary pressure, so more efficient and effective mutagenesis can be achieved. There is also an advantage that it may be easy to select an effective mutation by confirming the growth by culture under selective pressure. Therefore, the present method can efficiently and simply produce a microorganism having an ability of assimilating a target factor The produced microorganism may be further modified by a genetic engineering technique to construct a system capable of producing a high-value-added compound. This makes it possible to convert the taken first factor into a useful substance. Hence, the microorganism produced by the present method can be a platform bacterium for producing various high-value-added molecules. Although the modification will vary depending on the type of useful molecule of interest, those skilled in the art can modify the microorganism using conventional genetic engineering techniques. For example, when the first factor is carbon dioxide, it may be possible to achieve both an effective reduction in greenhouse gases and an economic effect due to production of high-value-added molecules by using a $CO_2$-assimilating bacterium produced by the present method.

One example of a method to which the present invention is applied will be described with reference to FIG. 1. FIG. 1 shows a method in which microorganisms are plated in a plate medium and subjected to mutagenesis in the presence of a high concentration of carbon dioxide as the first factor. In FIG. 1, alphabetical letters represent a substance, instruments, and a device, and number symbols represent operations.

Specific configurations of FIG. 1 are as follows:
a) a solution containing a microorganism to be subjected to mutagenesis;
b) a plate medium in which the microorganism to be subjected to mutagenesis has been plated;
c) a device that emits electromagnetic waves such as ultraviolet rays (UV) having an ability to mutagenize the gene in the microorganism;
d) an incubator in which the $CO_2$ concentration can be adjusted, and the temperature and humidity can also be adjusted;
e) a plate medium removed from the incubator, when appeared colonies are confirmed, these colonies are collected;
f) a plate medium for cloning the colonies identified on the plate medium e) and seeding the colonies to confirm again whether they can be grown under a directed evolutionary pressure; and
g) an incubator in which the $CO_2$ concentration can be adjusted to confirm whether the collected colonies grow on the plate medium f) in a high-concentration $CO_2$ atmosphere, and the temperature and humidity can also be adjusted.

Specific operations shown in FIG. 1 are as follows:
0: an appropriate number of microorganisms are collected from the solution a) containing a microorganism to be subjected to mutagenesis, and uniformly plated on a plate medium;
1: the plate medium b) after plating is irradiated with electromagnetic waves from the device c) and cultured in a high-concentration $CO_2$ atmosphere for a sufficient time, then taken out, and the presence or absence of colonies is confirmed;
2: in a case where colonies are confirmed, the colonies are seeded again to clone colony cells; and
3: colonies generated under a directed evolutionary pressure in a high-concentration $CO_2$ atmosphere are collected, the confirmation as to whether the colonies grow under the same environment is performed again, and single cloning is carried out.

EXAMPLES

Hereinafter, specific examples of embodiments of the present invention will be described with reference to the drawings. However, it should be noted that these examples are merely examples for realizing the present invention, and do not limit the present invention.

Example 1

In this example, *Escherichia coli* was used as a microorganism, UV irradiation as mutagen was performed on an agar medium coated with an *Escherichia coli* suspension, and anaerobic (oxygen-free) culture was performed in a high-concentration carbon dioxide atmosphere to obtain a microorganism having a carbon dioxide-assimilating ability.

As *Escherichia coli*, BL-21 (DE3) pLysS competent cells (L 1195, Promega) were used. A plasmid pET-21a (69740, Novagen) carrying the gene sequences of a carbon dioxide-fixing enzyme (pyruvate carboxykinase) and a carbon dioxide transporter (bicA) which were appropriately combined and arranged with a T7 promoter sequence, and BL-21 (DE3) pLysS competent cells (L 1195, Promega) were transformed with the plasmid. 100 microliters (corresponding to $10^8$ cells of *Escherichia coli*) of *Escherichia coli* suspension with an OD600 approximately equal to 1.2 were uniformly applied to a microplate-type petri dish on which an agar medium had been spread. In the composition of the agar medium, glucose was excluded from the SOC medium for use; the glucose is contained as a normal component in the SOC medium and is considered to be preferentially consumed by aerobic respiration of *Escherichia coli*.

Figure 2:
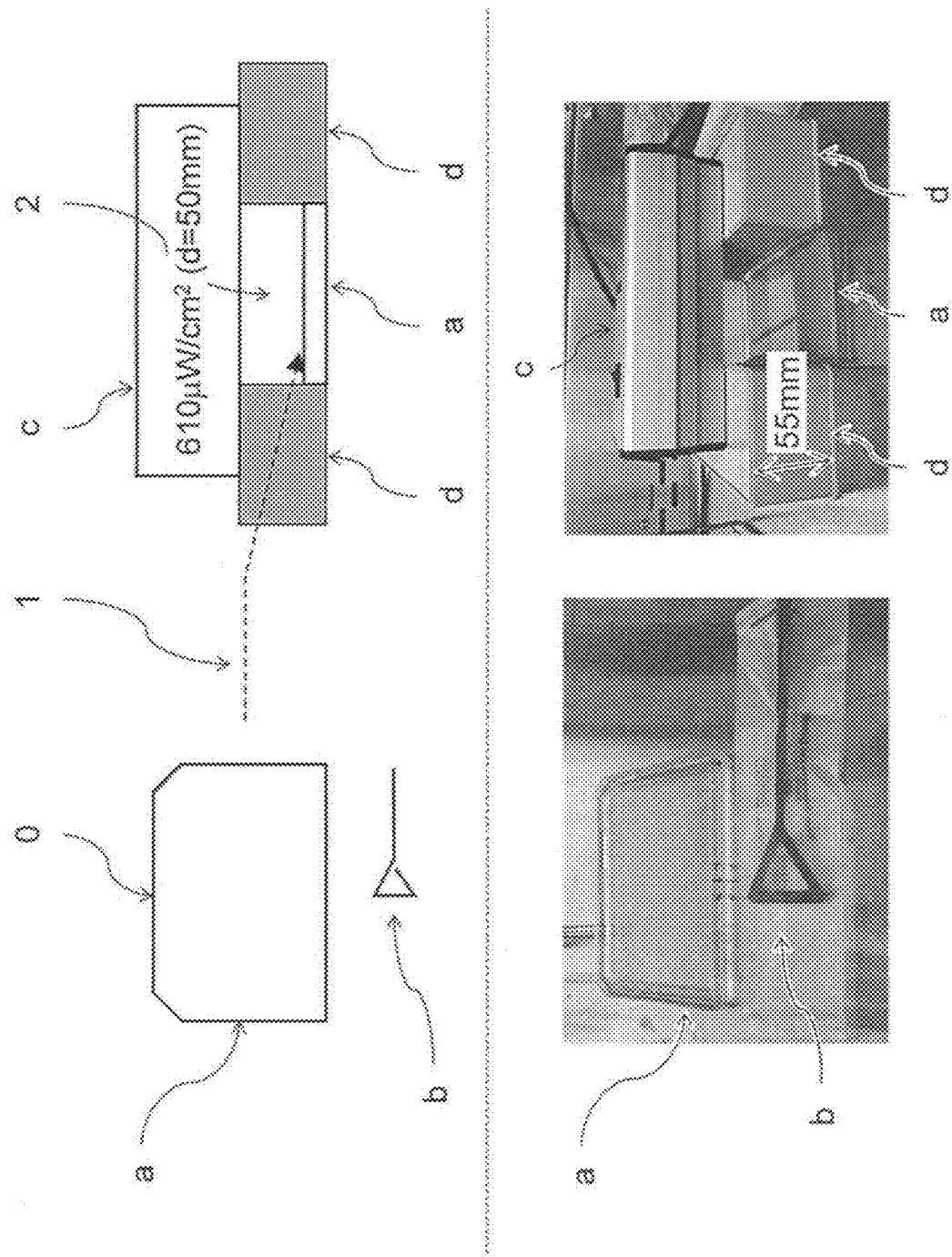
FIG. 2 shows configurations and operations of instruments and a device used in Example 1 (upper row) and photographs of the instruments and the device (lower row)

FIG. 2 shows configurations and operations of instruments and a device used in this example (upper row) and photographs of the instruments and the device (lower row). The positions of the instruments and the position of the device in the configurations in the upper row correspond to the positions of the instruments and the position of the device in the photographs in the lower row. In the figure, alphabetical letters represent a substance, the instruments, and the device, and number symbols represent operations.

Specific configurations of FIG. 2 are as follows:
a) a plate gel-like medium (a solution containing bacterial cells to be mutagenized is applied);
b) a spreading rod (spreader) (used to apply the solution);
c) an UV irradiation device (by which mutagenesis is performed); and
d) a stand (used to adjust the UV irradiation distance).

Specific operations shown in FIG. 2 are as follows:
0: a solution containing bacterial cells is applied to a plate gel-like medium;
1: the plate gel-like medium is put under the irradiation device to perform UV irradiation; and
2: the plate gel-like medium is irradiated with UV light from the irradiation device, culture is carried out in a sealed container containing a high concentration of carbon dioxide.

As shown in FIG. 2, the solution containing bacterial cells was uniformly applied to the plate gel-like medium using a spreading rod so that the number of bacterial cells was $10^8$ to $10^9$. In order to perform UV irradiation, the plate gel-like medium was put under a handy UV lamp (SUV-4, AS ONE Corporation) as the irradiation device. Ultraviolet light having a wavelength of 254 nm from the handy UV lamp was set to 10 $mJ/cm^2$, the gel was irradiated with the ultraviolet light at a distance of 50 mm from the irradiation device to the upper surface of the gel for 15 seconds (610 $\mu W/cm^2$, d=55 mm (SUV-4)). The UV-irradiated plate gel-like medium was placed in a sealed container, the container was filled with a gas which had been previously adjusted to 50% v/v $CO_2$ and 50% v/v $N_2$ by downward displacement of water using a gas from an $N_2$ line and a gas from a $CO_2$ cylinder, and anaerobic culture was performed at 37° C. for 18 to 20 hours. As a control group, a plate gel-like medium coated with an *Escherichia coli* suspension that had not been irradiated with UV light at all was similarly placed in another sealed container, the container was filled with a gas adjusted to 50% v/v $CO_2$ and 50% v/v $N_2$, and anaerobic culture was performed at 37° C. for 18 to 20 hours.

Figure 3:
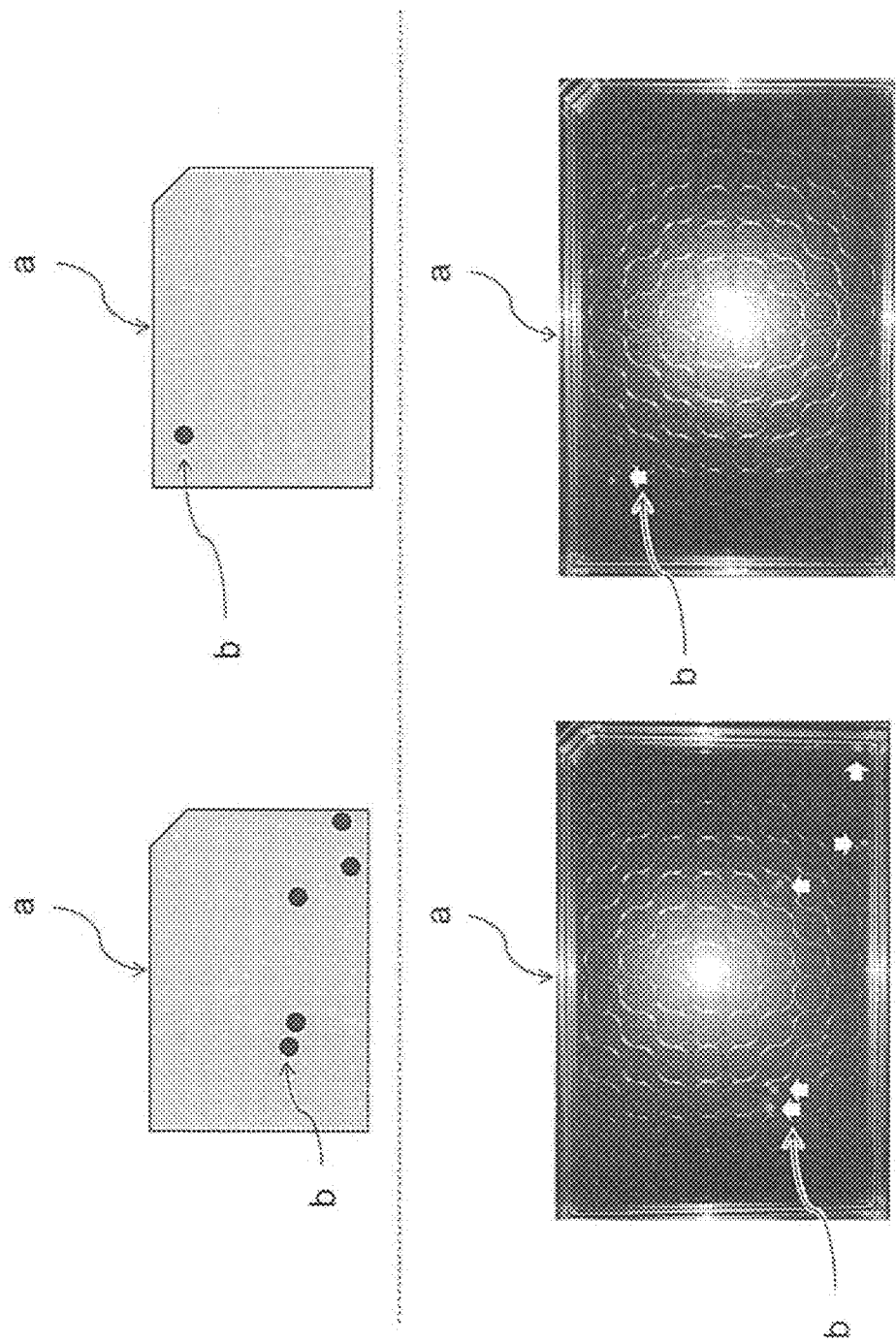
FIG. 3 shows positions of colonies obtained in Example 1 (upper row) and photographs of experimental results (lower row)

The results of the culture are shown in FIG. 3. FIG. 3 shows positions of the obtained colonies (upper row) and photographs of experimental results (lower row). The positions of the instruments and the positions of the generated phenomena in the configurations in the upper row correspond to the positions of the instruments and the positions of the generated phenomena in the photographs in the lower row.

In FIG. 3, alphanumeric characters "a" and "b" represent the following:

a: a plate gel-like medium coated with a solution containing mutagenized bacterial cells (left: a medium coated with bacterial cells obtained by mutagenesis of *Escherichia coli* into which a carbon dioxide-fixing enzyme and a carbon dioxide transporter have been introduced in a genetically engineered manner, and right: a medium coated with bacterial cells obtained by mutagenesis of wild-type *Escherichia coli*); and b: the resulting colonies (indicated by circles in the upper row, indicated by white arrows indicating actual colony positions in the lower row).

After the culturing, when the petri dish was observed, no colonies were obtained from the non-UV-irradiated group, whereas a plurality of colonies were observed from the UV-irradiated group (first trial: 6 colonies, second trial: 8 colonies) (FIG. 3). As a result, by colony selection in the high-concentration $CO_2$ environment used this time, it was possible to select bacterial cells into which a mutation corresponding to the environment had been introduced.

Example 2

In this example, it was confirmed whether or not the colonies obtained in Example 1 could be cultured in the same environment as that in which colony selection was performed after mutagenesis.

After mutagenesis by UV irradiation, in order to confirm whether the generated colonies actually grow in anaerobic conditions/-glucose, a small amount of each colony was collected with a needle, the inside of a test tube was replaced with $CO_2$, and the collected colonies were cultured in the test tube containing a SOC (-glucose) medium for 18 to 20 hours. A specific experimental procedure is shown in FIG. 4.

Specific instruments and a specific device in FIG. 4 are as follows:

a) culture tube to which a SOC medium containing no glucose component has been added;

b) a tube for performing downward replacement of carbon dioxide in order to discharge oxygen components in the culture tube; and c) a shaking culture incubator.

Specific operations shown in FIG. 4 are as follows:

0: colonies generated in a plate gel-like medium were transferred into a culture tube;

1: carbon dioxide was slowly injected to discharge oxygen components in the culture tube;

2: the tube was tightly sealed to prevent air from entering the tube; and

3: shake culture was performed at 37° C. for 20 hours in a shaking culture incubator.

The growth state of bacterial cells was observed by measuring the turbidity (OD 600). As a result, it was confirmed that the colonies 1, 2, 4, 5, and 6 among the colonies 1 to 6 generated in Example 1 were grown only under gas conditions of carbon dioxide without glucose under anaerobic conditions (Table 1).

TABLE 1

| Culture conditions | OD600 | | | | | |
|---|---|---|---|---|---|---|
| | Colony 1 | Colony 2 | Colony 3 | Colony 4 | Colony 5 | Colony 6 |
| SOC + Amp − Glucose − $O_2$ | 0.42 | 0.32 | 0.00 | 0.70 | 0.55 | 0.68 |
| SOC + Amp | 0.87 | 1.00 | 0.84 | 0.99 | 1.11 | 1.12 |

From the above Examples, it was confirmed that the combination of application of the bacterial cells to a plate gel-like medium immediately after mutagenesis by UV irradiation and culturing the colonies under a specific medium/gas condition was effective in obtaining a bacterial cell clone adapted to the intended environment. In particular, it was shown to be effective in the creation of *Escherichia coli* living under no oxygen and high carbon dioxide partial pressure.

In addition, the steps of (1) applying a solution corresponding to $10^8$ cells of *Escherichia coli*, (2) setting ultraviolet light having a wavelength of 254 nm to 10 $mJ/cm^2$, and (3) culturing with a gas adjusted to 50% v/v $CO_2$ and 50% v/v $N_2$, which had been performed in Example 1, were performed, as a result of which it was possible to establish a system capable of narrowing colonies to several levels.

There is a possibility that *Escherichia coli* using carbon dioxide as a carbon source and having a higher assimilation efficiency can be obtained by repeating the present method.

All of the scientific articles, patents, and published patent applications cited herein are hereby incorporated by reference.

What is claimed is:

1. A method of producing a microorganism having an ability of assimilating a first factor, the method comprising:
    subjecting a microorganism to random mutagenesis;
    culturing the microorganism in presence of a concentrated first factor to grow microorganism, and then selecting the grown microorganism on a solid medium on which the microorganism to be selected are expanded mechanically by a cell spreading device; and
    collecting all cloned colonies grown under the first factor by picking up each single colony of the colonies grown from a single cell after the culturing.

2. The method according to claim 1, wherein the subjecting of the microorganism to the random mutagenesis is performed in the presence of a concentrated first factor.

3. The method according to claim 1, wherein the first factor is at least one factor selected from the group consisting of a carbon source and a nitrogen source.

4. The method according to claim 3, wherein the carbon source comprises at least one carbon source selected from the group consisting of carbon dioxide, carbon monoxide, methane, methanol, acetic acid, and cellulose.

5. The method according to claim 1, wherein the first factor is carbon dioxide and the concentrated first factor has a concentration of 400 ppm to 5000 ppm.

6. The method according to claim 1, wherein the first factor is carbon dioxide, and the microorganism is cultured in a closed incubator containing carbon dioxide at a concentration of 0.5% or more.

7. The method according to claim 1, wherein the first factor is carbon dioxide, and the microorganism is cultured in a closed incubator containing carbon dioxide at a concentration of 5% or more.

8. The method according to claim 1, wherein when the first factor is a carbon source, the microorganism is cultured in a medium containing no carbon source other than the first factor.

9. The method according to claim 1, wherein the microorganism is cultured in absence of oxygen or in presence of oxygen.

10. The method according to claim 1, further comprising plating the microorganism on a plate medium before the subjecting of the microorganism to the random mutagenesis.

11. The method according to claim 1, wherein the subjecting of the microorganism to the random mutagenesis is performed by at least one selected from the group consisting of ultraviolet (UV) irradiation, gamma irradiation, ionizing radiation irradiation, X-ray irradiation, and addition of chemical mutagens.

12. The method according to claim 1, further comprising:
  recovering the selected microorganism; and
  culturing the microorganism again in the presence of the concentrated first factor.

13. The method according to claim 1, wherein the microorganism is at least one of eubacteria, gram-negative bacteria, gram-positive bacteria, cyanobacteria, archaea, and fungi.

14. The method according to claim 1, wherein the microorganism is *Escherichia coli*.

15. The method according to claim 1, wherein the microorganism is a microorganism into which a genetic mutation involved in metabolism of the first factor has been introduced before the random mutagenesis.

* * * * *